US006409771B2

(12) United States Patent
Damhus et al.

(10) Patent No.: US 6,409,771 B2
(45) Date of Patent: Jun. 25, 2002

(54) PROCESS FOR REMOVAL OF EXCESS DYE FROM PRINTED OR DYED FABRIC OR YARN

(75) Inventors: Ture Damhus, Copenhagen (DK); Uwe Vogt, Monheim (DE); Palle Schneider, Lynge (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/853,843

(22) Filed: May 11, 2001

Related U.S. Application Data

(62) Division of application No. 09/500,195, filed on Feb. 8, 2000, now Pat. No. 6,248,134, which is a division of application No. 09/221,653, filed on Dec. 23, 1998, now Pat. No. 6,048,367.
(60) Provisional application No. 60/071,184, filed on Jan. 12, 1998.

(30) Foreign Application Priority Data

Dec. 23, 1997 (DK) .................................. 1526/97

(51) Int. Cl.[7] .............................. D06L 3/02; D06L 3/11
(52) U.S. Cl. ...................... 8/111; 8/102; 8/401; 8/573; 8/137; 8/138; 510/281; 510/321; 510/393; 548/259

(58) Field of Search ................................. 510/281, 321, 510/393; 8/111, 102, 401, 573, 137, 138; 548/259

(56) References Cited

U.S. PATENT DOCUMENTS

| 5,948,122 A | * | 9/1999 | Xu et al. ........................ 8/401 |
| 6,048,367 A | * | 4/2000 | Damhus et al. ................. 8/111 |
| 6,129,769 A | * | 10/2000 | Xu et al. ........................ 8/401 |
| 6,248,134 B1 | * | 6/2001 | Damhus et al. ................. 8/111 |

FOREIGN PATENT DOCUMENTS

| WO | WO 92/18687 | * 10/1992 |
| WO | WO 94/29425 | 12/1994 |

* cited by examiner

*Primary Examiner*—Mark Kopec
*Assistant Examiner*—Brian P. Mruk
(74) *Attorney, Agent, or Firm*—Jason I. Garbell; Elias J. Lambiris

(57) ABSTRACT

The present invention provides a process for removal of excess dye from newly manufactured printed or dyed fabric or yarn, comprising treatment with a rinse liquor comprising at least one enzyme selected from the group consisting of enzymes exhibiting peroxidase activity or laccase activity, an oxidation agent, and at least one mediator comprising N-hydroxyacetanilide.

21 Claims, No Drawings

PROCESS FOR REMOVAL OF EXCESS DYE FROM PRINTED OR DYED FABRIC OR YARN

CROSS-REFERENCE TO RELATED APPLICATIONS

This is a divisional application of application Ser. No. 09/500,195 filed Feb. 8, 2000, which is a divisional application of application Ser. No. 09/221,653 filed Dec. 23, 1998 and claims priority of Danish application No. 1526/97 filed Dec. 23, 1997 and of U.S. provisional application No. 60/071,184 filed Jan. 12, 1998, the contents of which are fully incorporated herein by reference.

BACKGROUND OF THE INVENTION

1. Field of the Invention

The present invention relates to a novel method of removing excess dye from newly printed or dyed fabric or yarn as well as a system and a composition for use in the method.

2. Description of Related Art

Printing and dyeing of textiles is carried out by applying dyes to the textile by any appropriate method for binding the dyestuff to the fibres in the textiles. Excess soluble dyestuff not bound to the fibres must be removed after dyeing to ensure fastness of the dyed textiles and to prevent unwanted dye transfer during laundering of the textiles by the consumer.

Generally, a large amount of water is required for complete removal of excess dye. In a conventional process the printed or dyed textile is first rinsed with cold water, then washed at high temperature with the addition of a suitable additive to decrease back-staining, like poly (vinylpyrrolidone) (PVP). The process is repeated until a satisfactory amount of dyestuff (and thickeners) has been removed. PVP can be added to reduce back-staining during rinsing, but this compound does not bleach the dye and is relatively expensive. Furthermore, the waste liquor from a conventional process tends to be strongly colored and may represent a disposal problem, which is not reduced by the use of PVP.

WO 92/18687 discloses a method of bleaching excess dye from printed or dyed fabric by treating with a liquor containing an enzyme exhibiting peroxidase activity or oxidase activity, an $O_2$ or $H_2O_2$ source as applicable, and optionally an additional oxidizable substrate, such as a metal ion, a halide ion or an organic compound, such as a phenol.

However, the concentrations of such additional substrates necessary for enzymatically bleaching the excess dye in the rinse liquor may present a risk of bleaching the dyed textiles themselves.

Accordingly, it is an object of the present invention to provide a method for removing or bleaching excess dye without bleaching the dyed textile This is achieved by a process for removal of excess dye from newly manufactured printed or dyed fabric or yarn comprising treatment with a rinse liquor comprising

- at least one enzyme selected from the group consisting of enzymes exhibiting peroxidase activity or laccase activity,
- an oxidation agent, and
- at least one mediator selected from the group consisting of aliphatic, cyclo-aliphatic, heterocyclic or aromatic compounds containing the moiety >N—OH, and
- optionally additives.

In the present invention the term "mediator" means an additional oxidizable substance improving the bleaching performance.

By suitable combination of mediator and enzyme it is possible to avoid bleaching of the dyed textile while bleaching dyes in solution, thereby reducing the amount of unbleached dye deposited on the fibres and thus increasing the wet fastness of the dyed or printed textile.

By this process it is furthermore possible to reduce the number of rinsing steps and the temperature of the rinsing water in the rinsing steps compared to the conventional processes, thereby saving energy and costs.

Another object of the present invention is a system for removal of excess dye from newly manufactured printed or dyed fabric or yarn, which is a multi-component system comprising at least one enzyme selected from the group consisting of enzymes exhibiting peroxidase activity or laccase activity, an oxidation agent, and at least one mediator selected from the group consisting of aliphatic, cyclo-aliphatic, heterocyclic or aromatic compounds containing the moiety >N—OH, and optionally additives, such as rinsing additives.

The components of the system may be combined as a solution, a slurry or granulates depending on the specific enzymes and mediators selected.

A further object of the present invention is the use of the components specified above for the preparation of a multi-component system for removal of excess dye or print from newly manufactured fabric or yarn.

DETAILED DESCRIPTION OF THE INVENTION

Fabric or Yarn

The process of the invention is applicable to all types of textile materials, both natural fibres and synthetic fibres as well as blends thereof. Typical examples are cellulosic fibres (cotton and flax), modified cellulose fibres (e.g. acetate and triacetate), protein fibres (e.g. wool and silk), polyamide fibres (e.g. nylon 6 and 6,6), polyester fibres (e.g. poly (ethylene terephthalate)) and acrylic fibres.

The process of the invention may be applied to dyed yarn, to knitted, woven or non-woven fabric, or to garments made from dyed and/or printed fabric, especially garments made from differently colored material.

Printing Method

The process of the invention is suited for excess dye bleaching after any kind of textile printing. Examples of commonly used techniques are printing on a Rotation film, a Rouleaux, a Flash film, or a Transfer film device. After printing the dye is fixed on the textile by e.g. steaming or treatment with hot air.

Dyeing Method

The process of the invention is suited for excess dye bleaching after any kind of dyeing. The dyeing of textiles is for example carried out by passing the fabric through a concentrated solution of dye, followed by storage of the wet fabric in a vapour tight enclosure to permit time for diffusion and reaction of the dye with the fabric substrate prior to rinsing off un-reacted dye. Alternatively, the dye may be fixed by subsequent steaming of the textile prior to rinsing.

The process applies to any kind of dyes, such as reactive dyes.

Enzyme

Enzymes exhibiting peroxidase activity or laccase activity are those which by using hydrogen peroxide or molecular oxygen, respectively are capable of oxidising a variety of compounds, such as phenols and aromatic amines.

According to the invention the concentration of enzyme is 0.005 to 5 mg enzyme protein per 1 of rinse liquor, preferably, 0.02 to 2 mg enzyme protein per l of rinse liquor, more preferably 0.05 to 1 mg enzyme protein per l of rinse liquor. According to the liquor ratio, this may be translated to dosages of enzyme per kg of fabric, e.g. at a liquor ratio of 10:1, the most preferred enzyme dosage is from 0.5 to 10 mg enzyme per kg of textile fabric.

Peroxidase Activity Exhibiting Enzymes

An enzyme exhibiting peroxidase activity may be any peroxidase comprised by the enzyme classification (EC 1.11.1.7), or a haloperoxidase, such as a chloride peroxidase (EC 1.11.1.10) or any fragment or synthetic or semisynthetic derivatives thereof exhibiting enzymatic activity (e.g. porphyrin ring systems or microperoxidases, cf. e.g. U.S. Pat. No. 4,077,768, EP 537 381, WO 91/05858 and WO 92/16634). Such enzymes are known from microbial, plant and animal origins.

Preferably, the peroxidase employed in the method of the invention is producible by plants (e.g. horseradish or soybean peroxidase), in particular soybean peroxidase, or by microorganisms, such as fungi (including filamentous fungi and yeasts) or bacteria.

Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular Coprinus cinereus f. microsporus (IFO 8371), *Coprinus macrorhizus, Phanerochaete chrysosporium* (e.g. NA-12) or Trametes (some classes previously called Polyporus have been renamed to Trametes), e.g., *T. versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g., *Streptomyces spheroides* (ATTC 23965), *Streptomyces thermoviolaceus* (IFO 12382) or *Streptoverticillum verticillium* ssp. verticillium.

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g., *M. virescens*.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase, and recovering the peroxidase from the culture.

Particularly, a recombinantly produced peroxidase is a peroxidase derived from a Coprinus sp., in particular *C. macrorhizus* or *C. cinereus* according to WO 92/16634, or a variant thereof.

In the context of this invention, peroxidase acting compounds comprise peroxidase active fragments derived from cytochromes, hemoglobin or peroxidase enzymes, and synthetic or semisynthetic derivatives thereof, e.g. iron complexes of porphyrin or phthalocyanine and derivatives thereof.

Laccase and Laccase Related Enzymes

In the context of this invention, the term "enzymes exhibiting laccase activity" means laccases and laccase related enzymes, such as any laccase comprised by the enzyme classification (EC 1.10.3.2), any catechol oxidase comprised by the enzyme classification (EC 1.10.3.1), any bilirubin oxidase comprised by the enzyme classification (EC 1.3.3.5) or any monophenol monooxygenase comprised by the enzyme classification (EC 1.14.99.1).

The laccases are known from microbial and plant origin. The microbial laccases may be derived from bacteria or fungi (including filamentous fungi and yeasts) and suitable examples include a laccase derivable from a strain of Aspergillus, Neurospora, e.g., *N. crassa*, Podospora, Botrytis, Collybia, Fomes, Lentinus, Pleurotus, Trametes, e.g., *T. villosa* and *T. versicolor*, Rhizoctonia, e.g., *R. solani*, Coprinus, e.g. *C. plicatilis* and *C. cinereus*, Psatyrella, Myceliophthora, e.g. *M. thermophila*, Schytalidium, Polyporus, e.g., *P. pinsitus*, Phlebia, e.g., *P. radiata* (WO 92/01046), or Coriolus, e.g., *C. hirsutus* (JP 2-238885), in particular a laccase derivable from a strain of Fomes, Trametes, Rhizoctonia, Coprinus, Myceliophthora, Schytalidium, or Polyporus.

The laccase or the laccase related enzyme may furthermore be one which is producible by a method comprising cultivating a host cell transformed with a recombinant DNA vector which carries a DNA sequence encoding said laccase as well as DNA sequences encoding functions permitting the expression of the DNA sequence encoding the laccase, in a culture medium under conditions permitting the expression of the laccase, and recovering the laccase from the culture.

Oxidation Agent

If the oxidizing enzyme requires a source of hydrogen peroxide, the source may be hydrogen peroxide or a hydrogen peroxide precursor for in situ production of hydrogen peroxide, e.g., a percarbonate or a perborate, a persulfate, such as a trioxo(peroxo)sulfate or a $\mu$-peroxo-bis (trioxosulfate), a hydrogen peroxide-urea addition compound, a peroxycarboxylic acid or a salt thereof or a hydrogen peroxide generating enzyme system, e.g., an oxidase and a substrate for the oxidase, e.g. an amino acid oxidase and a suitable amino acid.

Hydrogen peroxide may be added at the beginning of or during the process, e.g., in a concentration corresponding to 0.01–50 mM $H_2O_2$, preferably 0.1 to 5 mM.

If the oxidizing enzyme requires molecular oxygen, molecular oxygen from the atmosphere will usually be present in sufficient quantity. Otherwise pure $O_2$ may be led to the rinse liquor, or an $O_2$ generating enzymatic system, e.g. a system based on hydrogen peroxide and a catalase, may be added.

Mediator

According to the invention at least one mediator selected from the group consisting of aliphatic, cyclo-aliphatic, heterocyclic or aromatic compounds containing the moiety >N—OH is added to the rinse liquor. In a preferred embodiment of the invention the mediator is a compound of formula I:

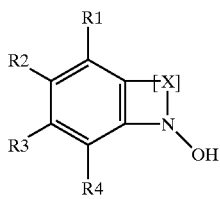

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_2$ alkyl), aryl, in particular phenyl, sulfo, aminosulfonyl, carbamoyl, phosphono, phosphonooxy, and salts and esters thereof, [X] is a group from (—N=N—), (—N=$CR^6$—)$_m$, (—$CR^7$=$CR^8$—)$_m$, and m is 1 or 2.

In a more preferred embodiment of the invention the mediator is a compound of formula II.

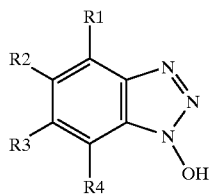

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_{11}$–C–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof.

The mediator may also be a salt or an ester of formula I or II.%

Further preferred mediators are oxoderivatives and N-hydroxy derivatives of heterocyclic compounds and oximes of oxo- and formyl-derivatives of heterocyclic compounds, said heterocyclic compounds including five-membered nitrogen-containing heterocycles, in particular pyrrol, pyrazole and imidazole and their hydrogenated counterparts (e.g. pyrrolidine) as well as triazoles, such as 1,2,4-triazole; six-membered nitrogen-containing heterocycles, in particular mono-, di- and triazinanes (such as piperidine and piperazine), morpholine and their unsaturated counterparts (e.g. pyridine and pyrimidine); and condensed heterocycles containing the above heterocycles as substructures, e.g. indole, benzothiazole, quinoline and benzoazepine.

Examples of preferred mediators from these classes of compounds are pyridine aldoximes; N-hydroxypyrrolidinediones such as N-hydroxysuccinimide and N-hydroxyphthalimide; 3,4-dihydro-3-hydroxybenzo[1,2,3]triazine-4-one; formaldoxime trimer (N,N',N"-trihydroxy-1,3,5-triazinane); and violuric acid (1,3-diazinane-2,4,5,6-tetrone-5-oxime).

Still further mediators which may be applied in the invention include oximes of oxo- and formyl-derivatives of aromatic compounds, such as benzoquinone dioxime and salicylaldoxime (2-hydroxybenzaldehyde oxime), and N-hydroxyamides and N-hydroxyanilides, such as N-hydroxyacetanilide.

Preferred mediators are selected from the group consisting of 1-hydroxybenzotriazole; 1-hydroxybenzotriazole hydrate; 1-hydroxybenzotriazole sodium salt; 1-hydroxybenzotriazole potassium salt; 1-hydroxybenzotriazole lithium salt; 1-hydroxybenzotriazole ammonium salt; 1-hydroxybenzotriazole calcium salt; 1-hydroxybenzotriazole magnesium salt; and 1-hydroxybenzotriazole-6-sulphonic acid.

A particularly preferred mediator is 1-hydroxybenzotriazole.

All the specifications of N-hydroxy compounds above are understood to include tautomeric forms such as N-oxides whenever relevant.

Usually, the concentration of mediator in the rinse liquor is from 0.1 $\mu$M to 50 mM, preferably 1 $\mu$M to 1 mM, more preferably 10 $\mu$M to 0.5 mM.

Additives

The rinse liquor may comprise further additives, such as surfactants and/or water conditioning agents.

Multi-component System

In order to carry out the process described above a multi-component system is added to the rinse liquor in at least one of the rinsing steps.

The components of the multi-component system may individually be in one of several product forms, such as a slurry, a solution or a granulate.

In one embodiment of the invention two components are mixed in the represented form, such as a co-granulate, a solution or a slurry comprising enzyme and mediator.

In cases of co-granulates, the co-granulate may comprise at least one enzyme and at least one mediator. Another example of a co-granulate is a granulate comprising at least two different enzymes and optionally at least one mediator.

In a further embodiment the system is a mixture of granulates wherein the component(s) in one granulate is(are) enzyme(s) and the component(s) in another granulate is(are) mediator(s).

According to the present invention a preferred multi-component system comprises at least one enzyme selected from the group consisting of enzymes exhibiting peroxidase activity or laccase activity, optionally an oxidation agent, and at least one mediator selected from the group consisting of aliphatic, cyclo-aliphatic, heterocyclic or aromatic compounds containing the moiety >N—OH as described above, and optionally additives, such as rinsing additives.

The enzymes exhibiting peroxidase activity or laccase activity are preferably as described above.

The system may comprise an oxidation agent, but in cases where the enzyme is an enzyme exhibiting laccase activity, molecular oxygen from the atmosphere is normally sufficient, and the system used will not comprise an oxidation agent. However, when the enzymes used require addition of an oxidation agent those are as described above. In all cases wherein a $H_2O_2$ source is the oxidation agent the enzyme and oxidation agent may not be mixed before use.

The mediator is as described above, in a preferred embodiment the mediator is selected from the group consisting of oxoderivatives and N-hydroxy derivatives of heterocyclic compounds and oximes of oxo- and formyl-derivatives of heterocyclic compounds, said heterocyclic compounds including five-membered nitrogen-containing heterocycles, in particular pyrrol, pyrazole and imidazole and their hydrogenated counterparts (e.g. pyrrolidine) as well as triazoles, such as 1,2,4-triazole; six-membered nitrogen-containing heterocycles, in particular mono-, di- and triazinanes (such as piperidine and piperazine), morpholine and their unsaturated counterparts (e.g. pyridine and pyrimidine); and condensed heterocycles containing the above heterocycles as substructures, e.g. indole, benzothiazole, quinoline and benzoazepine.

Examples of preferred mediators from these classes of compounds are pyridine aldoximes; N-hydroxypyrrolidinediones such as N-hydroxysuccinimide and N-hydroxyphthalimide; 3,4-dihydro-3-hydroxybenzo[1,2,3]triazine-4-one; formaldoxime trimer (N,N',N''-trihydroxy-1,3,5-triazinane); and violuric acid (1,3-diazinane-2,4,5,6-tetrone-5-oxime).

Still further mediators which may be applied in the invention include oximes of oxo- and formyl-derivatives of aromatic compounds, such as benzoquinone dioxime and salicylaldoxime (2-hydroxybenzaldehyde oxime), and N-hydroxyamides and N-hydroxyanilides, such as N-hydroxyacetanilide.

A particularly preferred mediator is 1-hydroxybenzotriazole.

All the specifications of N-hydroxy compounds above are understood to include tautomeric forms such as N-oxides whenever relevant.

A further aspect of the present invention is the use of components comprising at least one enzyme selected from the group consisting of enzymes exhibiting peroxidase activity or laccase activity, optionally an oxidation agent, and at least one mediator selected from the group consisting of aliphatic, cyclo-aliphatic, heterocyclic or aromatic compounds containing the moiety >N—OH, and optionally additives for the preparation of a multi-component system for removal of excess dye or print from newly manufactured fabric or yarn.

Process Conditions

The removal of excess dye, according to the invention, may comprise rinsing with rinse liquor in 2 to 6 rinsing steps, more preferred in 2 to 5 rinsing steps, even more preferred in 2 to 4 rinsing steps, in particular in 3 to 4 rinsing steps. The amount of rinsing steps is dependent on the concentration of the mediator and of the concentration of the peroxidase.

The multi-component system as defined according to this invention may be used in any of the rinsing steps performed, however it is preferably added in one of the last rinsing steps, in particular in the third or fourth rinsing step.

The process may be run in batch mode or continuous mode. The process may be applied on a winch, a beck, a jet dyer, an open-width washing machine, a J or U box, a steamer, or any other equipment available suitable for a rinsing process.

The process conditions must be chosen according to the characteristics of the enzyme in question. The temperature at the rinsing step comprising a multi-component system as defined above is preferably ranging from 40° C. to 80° C., such as from 50° C. to 70° C., and pH is typically in the range of 5.5–9.5, such as 6.5–9.

Fatness

Fastness (wet, crock, light, etc.) may be measured by various methods as known in the art. Wet fastness may be measured as described below. Colorfastness to crocking, which is designed to determine the amount of color transferred from the surface of colored materials to other surfaces by rubbing, may be measured according to AATCC Test Method 8–1996. Colorfastness to light, in which samples of the material to be tested and the agreed upon comparison standard(s) are exposed simultaneously to a light source under specified conditions, may be measured according to AATCC Test Method 16–1993.

Wet Fastness

The multi-component system as defined above is added to the rinsing liquor to prevent re-deposition of solubilized excess dye by bleaching it in solution.

The wet fastness or water fastness reflects the degree to which this has successfully been achieved.

In the present invention the wet fastness is measured by the standard method (DIN 54 006). Briefly, the method comprises soaking a dyed fabric and pressing it together with swatches of white fabric. After separate drying of the fabrics, the swatches are evaluated for staining.

The degree of wet fastness is indicated on a scale, the higher number the better wet fastness. 1 means very low wet fastness, whereas 5 means very high wet fastness.

Color Measurement (Example 5)

A Gretag-Mecbath Color Eye 3100 was used according to the manufacturer's instructions to evaluate the chromaticity using the change in the color space coordinates L*a*b* (CIELAB-system), where as usual:

L* gives the change in white/black on a scale from 0 to 100, and a decrease in L* means an increase in black color (decrease in white color) and an increase in L* means an increase in white color (decrease in black color).

a* gives the change in red/green, and a decrease in a* means an increase in green color (decrease in red color), and an increase in a* means an increase in red color (decrease in green color).

b* gives the change in blue/yellow, and a decrease in b* means an increase in blue color (decrease in yellow color), and an increase in b* means an increase in yellow color (decrease in blue color) (Vide WO 96/12846 NOVO).

The Gretag-Macbeth Color Eye 3100 was operated in the L*a*b* color space. The light source was D65 standard light. The software used for evaluation was Optiview Quality Control 1.7c. The observation angle was 10°. The instrument was calibrated using a Macbeth calibration plate (white). Each result was an average of 10 measurements. Fabric rinsed without enzyme and mediator was measured and the coordinates L*a*b* were calculated and entered as a reference. The coordinates of the samples were then for each of L*, a*, b* calculated as the difference (Δ) of the average of the measurements on each swatch from the reference value.

The present invention is further illustrated in the following examples which are not in any way intended to limit the scope of the invention as claimed.

EXAMPLE 1

Reactive Dyeing of Cotton Fabric Followed by an Enzymatic Rinsing Process

Knitted, bleached 100% cotton was dyed in a Mathis jet-dyer (laboratory scale jet dyeing machine) under the following conditions:

Water: softened water, 10 l/kg of fabric
Temperature: 50° C.
Dyestuff: 4% LEVAFIX Scarlet E-2GA (Reactive Red 123)
$Na_2SO_4$: 50 g/l
$Na_2CO_3$: 4 g/l
NaOH (32%): 2 ml/l
LEVEGAL RL: 1.0 g/l (levelling agent)
ERKANTOL NR: 1.0 g/l (wetting agent)
PERSOFTAL L: 1.0 g/l (crease-preventing agent)
RESPUMIT S: 1.0 g/l (antifoaming agent)
  LEVAFIX Scarlett E-2GA is a product of DyStar.
  LEVEGAL RL, ERKANTOL NR, PERSOFTAL L and RESPUMIT S are products of BAYER.

The dyeing process started at 50° C. by addition of dyestuff, $Na_2SO_4$, LEVEGAL RL, ERKANTOL NR, PERSOFTAL L and RESPUMIT S. $Na_2CO_3$ was added 30 minutes after start and NaOH 60 minutes after start. During the whole process the temperature was held at 50° C.

60 minutes after addition of NaOH the dyeing process was stopped by draining off the dyeing liquor, whereafter the rinsing process was started.

The rinsing process was carried out as follows:
First Rinsing Step
  Addition of fresh softened water; 10 l/kg fabric.
  Rinsing 10 minutes at 40° C.
  Draining the rinsing liquor.
Second Rinsing Step
  Addition of fresh softened water; 10 l/kg fabric.
  Addition of 10 ml/l of acetic acid (6% solution in water)
  Rinsing 20 minutes at 95° C.
  Draining the rinsing liquor.
Third Rinsing Step
  Addition of fresh softened water; 10 l/kg fabric.
  Addition of 5.0 ml/l of potassium phosphate buffer (1.0 M, pH=7.0)
  Rinsing 40 minutes at 60° C.
  Addition of 0.8 mg/l Peroxidase SP502, 55 mg/l (0.4 mM) HOBT and 39 mg/l (0.4 mM) $H_2O_2$ (35% solution in water)
  Rinsing 10 minutes at 60° C.
  Draining the rinsing liquor.

SP502 was a liquid preparation of recombinant *Coprinus cinereus* peroxidase supplied by Novo Nordisk A/S (produced as described in WO 92/16634). HOBT was 1-hydroxybenzotriazole ex Sigma.

The fabric was squeezed and dried. The wet fastness was determined according to DIN 54 006. The degree of fastness was found to be 3 (adjacent fabric cotton).

EXAMPLE 2

(For Comparison)
Conventional 3 Step Rinsing Process
The dyeing process was carried out as described in Example 1. The rinsing steps were carried out as follows.
First Rinsing Step
  Addition of fresh softened water; 10 l/kg fabric.
  Rinsing 10 minutes at 40° C.
  Draining the rinsing liquor.
Second Rinsing Step
  Addition of fresh softened water; 10 l/kg fabric.
  Rinsing 20 minutes at 95° C.
  Draining the rinsing liquor.
Third Rinsing Step
  Addition of fresh softened water; 10 l/kg fabric.
  Rinsing 10 minutes at 80° C.
  Draining the rinsing liquor.

The fabric was squeezed and dried. The wet fastness was determined according to DIN 54 006. The degree of fastness was found to be 2 (adjacent fabric cotton).

EXAMPLE 3

(For Comparison)
Conventional 4 Step Rinsing Process
The dyeing process was carried out as described in Example 1. The rinsing steps were carried out as follows.
First Rinsing Step
  Addition of fresh softened water; 10 l/kg fabric.
  Rinsing 10 minutes at 40° C.
  Draining the rinsing liquor.
Second Rinsing Step
  Addition of fresh softened water; 10 l/kg fabric.
  Rinsing 10 minutes at 70° C.
  Draining the rinsing liquor.
Third Rinsing Step
  Addition of fresh softened water; 10 l/kg fabric.
  Rinsing 20 minutes at 95° C.
  Draining the rinsing liquor.
Fourth Rinsing Step
  Addition of fresh softened water; 10 l/kg fabric.
  Rinsing 10 minutes at 40° C.
  Draining the rinsing liquor.

The fabric was squeezed and dried. The wet fastness was determined according to DIN 54 006. The degree of fastness was found to be 2–3 (adjacent fabric cotton).

EXAMPLE 4

(For Comparison)
Conventional 6 Step Rinsing Process
The dyeing process was carried out as described in Example 1. The rinsing steps were carried out as follows.
First Rinsing Step
  Addition of fresh softened water; 10 l/kg fabric.
  Rinsing 10 minutes at 40° C.
  Draining the rinsing liquor.
Second Rinsing Step
  Addition of fresh softened water; 10 l/kg fabric.
  Rinsing 10 minutes at 70° C.
  Draining the rinsing liquor.
Third Rinsing Step
  Addition of fresh softened water; 10 l/kg fabric.
  Rinsing 10 minutes at 70° C.
  Draining the rinsing liquor.
Fourth Rinsing Step
  Addition of fresh softened water; 10 l/kg fabric.
  Rinsing 20 minutes at 95° C.
  Draining the rinsing liquor.

Fifth Rinsing Step
  Addition of fresh softened water; 10 l/kg fabric.
  Rinsing 10 minutes at 70° C.
  Draining the rinsing liquor.
Sixth Rinsing Step
  Addition of fresh softened water; 10 l/kg fabric.
  Rinsing 10 minutes at 40° C.
  Draining the rinsing liquor.
  The fabric was squeezed and dried. The wet fastness was determined according to DIN 54006. The degree of fastness was found to be 3 (adjacent fabric cotton).
  Conclusion: The wet fastness 3 (corresponding to the conventional 6 step rinsing process) was also obtained by the process according to the invention (see Example 1), whereby a substantial amount of rinsing steps can be avoided (saving water and energy and process time).

EXAMPLE 5
Reactive Dyeing of Cotton Fabric Followed by Enzymatic Rinsing Processes Using two Different Mediators
  Knitted, bleached 100% cotton was dyed in a Mathis jet-dyer (laboratory scale jet dyeing machine) at the following conditions:
  Water: softened water, 10 l/kg of fabric
  Dyestuff:
    1% Remazol Yellow RR
    1% Remazol Red RR 1% Remazol Blue RR
  $Na_2SO_4$: 70 g/l
  $Na_2CO_3$: 5 g/l
  NaOH (32% in water): 3 ml/l
  LEVEGAL RL: 1.0 g/l (levelling agent)
  ERKANTOL NR: 1.0 g/l (wetting agent)
  PERSOFTAL L: 1.0 g/l (crease-preventing agent)
    Remazol Yellow RR, Remazol Red RR, and Remazol Blue RR are products of DyStar.
    LEVEGAL RL, ERKANTOL NR, and PERSOFTAL L are products of BAYER.
  The dyeing process started at 30° C. by addition of $Na_2CO_3$, NaOH (1 ml/l), $Na_2SO_4$, LEVEGAL RL, ERKANTOL NR, PERSOFTAL L. The dyestuffs were added 15 minutes after start. 30 minutes after start the temperature was increased up to 50° C. within 20 minutes. 30 minutes after reaching 50° C. the remaining NaOH (2 ml/l) was added. 45 minutes after the addition of NaOH (2 ml/l) the dyeing process was finished by draining off the dyeing liquor, whereafter the rinsing process was started.
  The following rinsing process was carried out for each mediator (1-hydroxybenzotriazole (according to the invention); and methyl syringate (comparison)):
First Rinsing Step
  Addition of fresh softened water; 10 l/kg fabric.
  Rinsing 10 minutes at 40° C.
  Draining the rinsing liquor.
Second Rinsing Step
  Addition of fresh softened water; 10 l/kg fabric.
  Addition of 10 ml/l of acetic acid (6% solution in water)
  Rinsing 20 minutes at 95° C.
  Draining the rinsing liquor.
Third Rinsing Step
  Addition of fresh softened water; 10 l/kg fabric.
  Addition of 5.0 ml/l of potassium phosphate buffer (1.0 M, pH=7.0)
  Rinsing 40 minutes at 60° C.
  Addition of 0.8 mg/l Peroxidase SP502, 0.4 mM mediator and 39 mg/l (0.4 mM) $H_2O_2$ (35% solution in water)
  Rinsing 10 minutes at 60° C.
  Draining the rinsing liquor.
  SP502 was a liquid preparation of recombinant *Coprinus cinereus* peroxidase supplied by Novo Nordisk A/S.
  The fabric was squeezed and dried. A color measurement was performed using a color measuring instrument (Gretag-Macbeth Color Eye 3100) as described above.
Results
  Mediator: 1-hydroxybenzotriazole
  $\Delta L^*=0.756$
  $\Delta a^*=0.045$
  $\Delta b^*=0.022$
  Mediator: Methyl syringate
  $\Delta L^*=3.142$
  $\Delta a^*=0.134$
  $\Delta b^*=0.834$
Conclusion: It can be seen that methyl syringate has a significant and undesired influence on the chromaticity of the fabric. The positive $\Delta b^*$ of 0.834 indicates a very strong and not acceptable increase in yellow color whereas a $\Delta b^*$ of 0.022 which is found for 1-hydroxybenzotriazole is negligible and not visible. It is seen that also $\Delta L^*$ and $\Delta a^*$ are significantly smaller in the treatment according to the invention than in the comparison treatment.

EXAMPLE 6
Enzymatic Bleaching of Soluble Dyes
  The dyes tested were Reactive Black 5 (Remazol Black B), Reactive Red 198 (Remazol Red RB), Reactive Blue 220(Remazol Brilliant Blue BB), Reactive Blue 21 (Remazol Turquoise Blue G), and Reactive Orange 107 (Remazol Golden Yellow RNL), all ex Dystar. All dyes were dissolved in a 0.5 mM sodium phosphate buffer (pH 7.0) to an initial absorbance of approximately 0.4 at the wavelength $\lambda$max of maximum absorbance within the visible range. The solutions were then placed in a thermostated quartz cell in a HP 8453 diode array spectrophotometer, the three components of the enzymatic oxidation system were added (CiP to 0.2 mg/l, HOBT to 100 $\mu$M, hydrogen peroxide to 200 $\mu$M), and the absorbance ABS($\lambda$max) at $\lambda$max monitored over time. The degree of bleaching at 5 min, i.e. the decrease in ABS($\lambda$max) over 5 min divided by ABS($\lambda$max) at t=0, is shown below, measured at three temperatures.
Degree of Bleaching at 5 min(%):
Reactive Black 5 ($\lambda$max=596 nm)
  79 (60° C.); 82 (70° C.); 72 (80° C.);
Reactive Red 198 ($\lambda$max=517 nm):
  97 (60° C.); 100 (70° C.); 88 (80° C);
Reactive Blue 220 ($\lambda$max=608 nm):
  100 (60° C.); 98 (70° C.); 30 (80° C.);
Reactive Blue 21 ($\lambda$max=663 nm):
  100 (60° C.); 88 (70° C.); 61 (80° C.);
Reactive Orange 107 ($\lambda$max=408 nm):
  90 (60° C.); 67 (70° C.); 36 (80° C.).
  This example demonstrates that one of the preferred mediators according to the invention, HOBT (1-hydroxybenzotriazole), combined with *Coprinus cinereus* peroxidase (CiP) and hydrogen peroxide, provides high degrees of bleaching of soluble dyes in short time with a range of reactive dyes.
  What is claimed is:
  1. A process for removal of excess dye from newly manufactured printed or dyed fabric or yarn, comprising treatment with a rinse liquor comprising (a) at least one enzyme exhibiting peroxidase activity or laccase activity, (b) an oxidation agent, and (c) N-hydroxyacetanilide.

2. The process of claim 1, wherein the rinse liquor further comprises additives.

3. The process of claim 1, wherein the enzyme is a laccase (EC 1.10.3.2), catechol oxidase (EC 1.10.3.1), bilirubin oxidase (EC 1.3.3.5), a peroxidase (EC 1.11.1.7), or haloperoxidase.

4. The process of claim 3, wherein the enzyme is a chloride peroxidase (EC 1.11.1.10).

5. The process of claim 3, wherein the peroxidase is derived from a strain of Coprinus or from soybean.

6. The process of claim 3, wherein the laccase is derived from a strain of Fomes, Trametes, Rhizoctonia, Coprinus, Myceliophthora, Schytalidium, or Polyporus.

7. The process of claim 1, wherein the amount of enzyme is 0.005 to 5 mg enzyme protein per liter of rinse liquor.

8. The process of claim 1, wherein the oxidation agent is a $H_2O_2$ source.

9. The process of claim 1, wherein the oxidation agent is an $O_2$ source.

10. The process of claim 1, wherein the concentration of N-hydroxyacetanilide in the rinse liquor is from 0.1 µM to 50 mM.

11. The process of claim 10, wherein the concentration of N-hydroxyacetanilide in the rinse liquor is from 1 µM to 1 mM.

12. The process of claim 11, wherein the concentration of N-hydroxyacetanilide in the rinse liquor is from 10 µM to 0.5 mM.

13. The process of claim 2, wherein the additives are surfactants and/or water conditioning agents.

14. The process of claim 1, wherein the dye or print is a reactive dye.

15. A system for removal of excess dye from newly manufactured printed or dyed fabric or yarn, which is a multi-component system comprising (a) at least one enzyme exhibiting peroxidase activity or laccase activity, (b) optionally an oxidation agent, (c) a mediator comprising N-hydroxyacetanilide, and (d) optionally additives.

16. The system of claim 15, wherein the enzyme is a laccase (EC 1.10.3.2), a catechol oxidase (EC 1.10.3.1), a bilirubin oxidase (EC 1.3.3.5), a peroxidase (EC 1.11.1.7), or a haloperoxidase.

17. The system of claim 16, wherein the enzyme is a chloride peroxidase (EC 1.11.1.10).

18. The system of claim 15, wherein one component is a solution comprising the enzyme(s) and the mediator(s).

19. The system of claim 15, wherein one component is a slurry comprising the enzyme(s) and the mediator(s).

20. The system of claim 15, wherein one component is a granulate comprising the enzyme(s) and the mediator(s).

21. The system of claim 15, wherein one component is a granulate comprising the enzyme(s) and another component is a granulate comprising the mediator(s).

* * * * *